United States Patent

O'Neill et al.

Patent Number: 5,084,033
Date of Patent: Jan. 28, 1992

[54] ARTERIAL CANNULA TIP AND METHOD OF MANUFACTURE

[75] Inventors: William G. O'Neill, Ann Arbor; Erin J. Lindsay, Dexter, both of Mich.

[73] Assignee: Minnesota Mining and Manufacturing Company, St. Paul, Minn.

[21] Appl. No.: 492,604

[22] Filed: Mar. 12, 1990

[51] Int. Cl.$^5$ .............................. A61M 25/00
[52] U.S. Cl. ................................ 604/264; 138/39; 604/282
[58] Field of Search ............... 138/77; 604/264, 272, 604/280, 281, 282, 93, 96, 51–54

[56] References Cited

U.S. PATENT DOCUMENTS

| | | | |
|---|---|---|---|
| 2,899,959 | 8/1959 | Ginsburg | 604/272 X |
| 3,623,511 | 11/1971 | Levin | 138/39 |
| 4,002,174 | 1/1977 | Reed et al. | 604/272 X |
| 4,508,535 | 4/1985 | Joh et al. | 604/282 |
| 4,710,181 | 12/1987 | Fuqua | 604/280 |
| 4,909,787 | 3/1990 | Danforth | 604/95 |

OTHER PUBLICATIONS

Two brochures for "Sarns D$^4$" brand cannula, 1988.
Brochure for "Argyle Thi Aortic Perfusion Cannula", undated.
Brochrue for Bard "Aortic Perfusion Cannulae", undated.
Brochure for Research Medical, Inc. "Aortic Perfusion Cannulae", undated.

Primary Examiner—John D. Yasko
Assistant Examiner—Adam J. Cermak
Attorney, Agent, or Firm—Gary L. Griswold; Walter N. Kirn; Stephen W. Bauer

[57] ABSTRACT

An improved arterial cannula tip of the type comprising a hollow tube having a bent inlet conduit, the improvement comprising constructing the cannula tip so that the wall of the cannula tip is thicker at the inside of the bend than in the surrounding areas. The cannula is preferably formed by taking a generally tubular blank having an area in which the wall of the blank is thicker than the surrounding areas, and bending the blank in this area of increased thickness. The blank may be formed by molding the blank in a mold with a core pin bent or configured to form the area of increased thickness on one side of the blank.

16 Claims, 1 Drawing Sheet

ARTERIAL CANNULA TIP AND METHOD OF MANUFACTURE

This invention relates to arterial cannulas, and in particular to improvements in the construction of and method of manufacture of the tips of such cannulas.

BACKGROUND OF THE INVENTION

An arterial cannula is used to route oxygenated blood from a heart-lung machine to a patient's ascending aorta. The tip of the cannula must be sufficiently rigid so that it can be inserted through the incision without a dilator, and so that once it is inserted in the aorta it resists kinking. However, it is usually desirable for the cannula tip to be sufficiently flexible to minimize tissue damage if the tip scrapes the wall of the aorta (although some surgeons prefer rigid stainless steel cannula tips). It is also important to make the inside diameter of the cannula tip as large as possible relative to the outside diameter to minimize the pressure drop through the cannula and to minimize blood damage.

One type of arterial cannula currently in use is the "SARNS D4" brand cannula sold by Sarns, Inc., of Ann Arbor, Mich., a subsidiary of the Minnesota Mining and Manufacturing Company of St. Paul, Minn. The tip of that cannula provides a desirable balance of rigidity and small pressure drop. The inlet conduit of that cannula tip is molded as a straight tube with a uniform wall thickness, which is then heated and bent. During the heat formation process the inside of the bend or the "chin" is subjected to high stresses, and sometimes wrinkles. This can cause weaknesses in the cannula tip, and a significant portion of the cannulas made this way must be rejected.

Other types of arterial cannulas include the cannula sold under the trade designation "ARGYLE THI AORTIC PERFUSION CANNULA" by the Sherwood Medical Company of St. Louis, Mo., and various arterial cannulas sold by C. R. Bard, Inc., of Murray Hill, N.J. It is believed that the Sherwood Medical Company produces its "ARGYLE THI" brand cannula by extrusion, and C. R. Bard produces their cannulas by repeatedly dipping the cannula tube into a molten elastomeric material until the desired wall thickness is achieved. Research Medical, Inc., of Salt Lake City, Utah, and DLP, Inc., of Grand Rapids, Mich., also produce arterial cannulas.

SUMMARY OF THE INVENTION

The present invention relates to an improved arterial cannula tip of the type comprising a hollow body that has an angled inlet conduit. Generally, the cannula tip of the present invention comprises a hollow tube with a bent inlet conduit which is constructed so that the wall is thicker at the inside of the bend than in the surrounding areas.

The present invention also relates to an improved method of manufacturing an arterial cannula tip of the type comprising a hollow tube that has an angled inlet conduit. Generally, the method of the present invention comprises forming a hollow tubular blank having an area of increased wall thickness, and bending the tubular blank at the area of increased wall thickness so that the area of increased wall thickness is at the inside of the bend.

The increased wall thickness at the inside of the bend reduces wrinkling of the arterial cannula tip and reduces variations in the strength of the cannula tip. Thus the improved method of making cannula tip according to this invention provides greater uniformity of cannula quality, and reduces the number of rejects. The improved cannulas have greater uniformity in strength and greater reliability, while maximizing the internal cross-sectional area for a given external diameter.

These and other advantages will be in part apparent and in part pointed out hereinafter.

BRIEF DESCRIPTION OF THE DRAWINGS

The invention will be further described with reference to the drawing wherein corresponding reference numerals indicate corresponding parts throughout the several views of the drawing, and wherein.

DETAILED DESCRIPTION OF A PREFERRED EMBODIMENT

Figure 1:
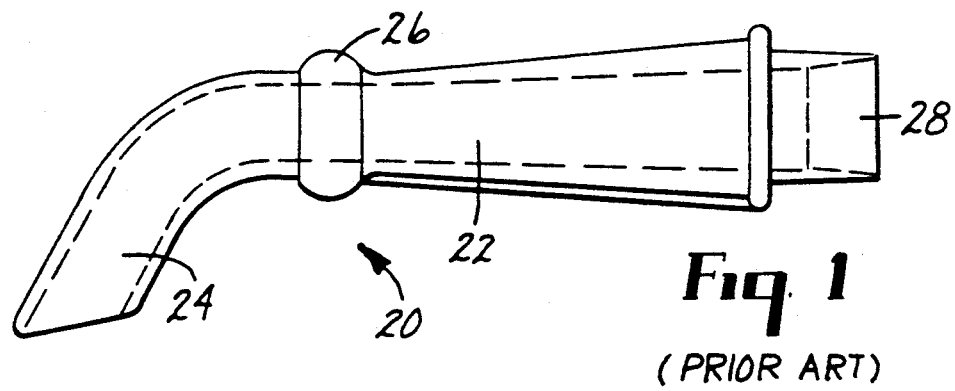
FIG. 1 is a side elevation view of a currently available arterial cannula tip.

An arterial cannula tip of the type presently available, indicated generally as 20, is shown in side elevation in FIG. 1. The cannula tip 20 comprises a tapered neck or body 22 and a bent inlet conduit 24. The inlet conduit 24 is preferably bent at an angle of between about 50 degrees and 68 degrees with respect to the axis of the body 22. The inlet conduit 24 is bent on a radius of between about 0.22 and 0.40 inches (5.6 mm and 10 mm), and more preferably at about 0.31 inches (7.9 mm). A raised circumferential band 26 separates the inlet conduit 24 from the tapered body 22. The end 28 of the body 22 opposite the inlet conduit 24 is adapted to connect the arterial cannula tip 20 to a conventional cannula tube (not shown).

Figure 3:
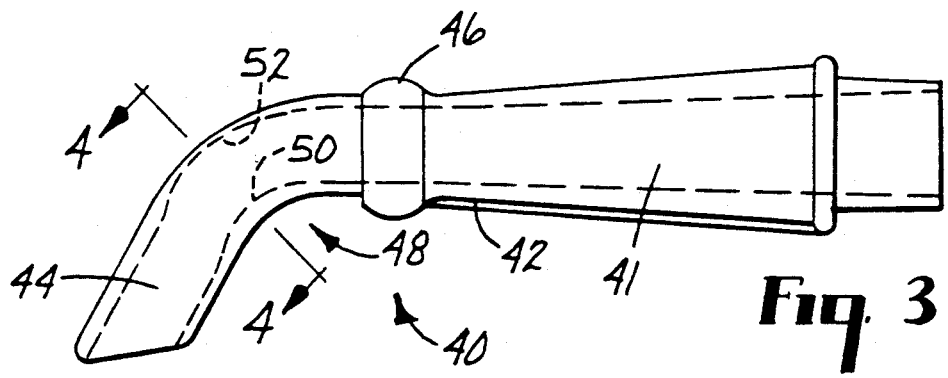
FIG. 3 is a side elevation view of an arterial cannula tip constructed according to the principles of the present invention.

An improved arterial cannula tip constructed according to the principles of the present invention, indicated generally as 40, is shown in side elevation in FIG. 3. Cannula tip 40 comprises a hollow tube 41 forming a tapered neck or body 42, a bent inlet conduit 44, and a raised circumferential band 46 separating the inlet conduit 44 from the body 42. The cannula tip 40 is constructed so that the wall of the inlet conduit 44 is thicker at the inside of the bend (which is indicated generally at 48). The wall of the inlet conduit 44 at the inside of the bend 48 might be about 40% thicker than the surrounding portions of the inlet conduit 44. While the wall thickness of inlet conduit 44 might average about 0.035 inches (890 micrometers), the wall thickness in the area 50 might be about 0.050 inches (1.3 mm).

Figure 2:
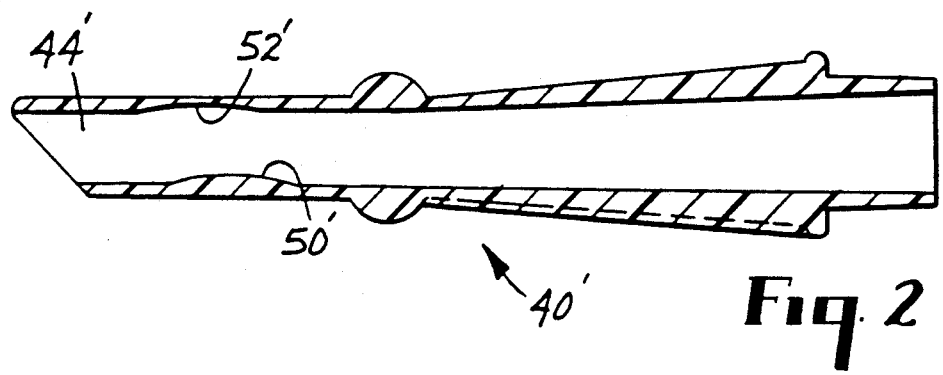
FIG. 2 is a longitudinal cross-sectional view of a tubular blank with an area of increased wall thickness for use in making arterial cannula tips according to this invention.

According to the improved method of making an arterial cannula tip 40 of the present invention, a cannula tip blank 40' (see FIG. 2) is formed with an area 50' of increased wall thickness. As discussed above, the thickness of the tubular blank in the area 50' might be 40% greater than the thickness of the surrounding portions of the inlet conduit 44' of the blank 40'. Thus, while the wall thickness of the inlet conduit 44' of the blank 40' might average about 0.035 inches (890 micrometers), the wall thickness in the area 50' might be about 0.050 inches (1.3 mm).

The blank 40' is preferably formed by molding. The area 50' of increased wall thickness may be (but is not necessarily) formed by bending the core pin of the mold used to form the hollow center of the blank 40'. If a bent core pin is used, then an area 52' of reduced wall thickness will be formed in the blank 40', opposite from area 50'. While the area 50' may have a thickness of about 0.050 inches (1.3 mm), area 52' might have a thickness of about 0.020 inches (510 micrometers), and the wall thickness of the rest of the inlet conduit 44' might average about 0.035 inches (890 micrometers). The bent core pin is preferably smoothly bent and contoured so that the area of increased wall thickness of the cannula tip 40 is smoothly contoured.

Alternatively the core pin could be configured to produce the area 50' of increased thickness. For example, the core pin may include a recessed portion (not shown), which will produce the desired area 50' of increased thickness. Such a recess may be formed by smoothly contoured walls so that the thickness of the blank 40' is increased gradually in area 50'.

Figure 4:
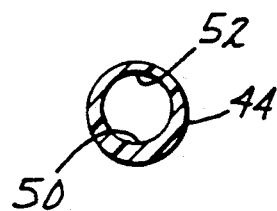
FIG. 4 is a cross-sectional view substantially along line 4—4 of FIG. 3.

The blank 40' is bent at the area 50' to form the angled inlet conduit 44, with the area 50 on the inside of the bend 48. The resulting cannula tip 40 has an area 50 of increased thickness at the inside of the bend 48, and depending on the method of forming the blank 40' may have a corresponding area 52 of decreased thickness at the outside of the bend, as illustrated in FIGS. 3 and 4. The relatively greater thickness in area 50 reduces buckling and wrinkling on the inside of the bend 48 that occurs when bending blanks of uniform cross section. This results in greater uniformity in cannula quality, and reduces the incidence of rejected cannulas. The inlet conduit 44 is preferably bent at an angle of between about 50 degrees and about 68 degrees with respect to the axis of the body 42 of the cannula tip 40, and more preferably at an angle of about 59 degrees. The inlet conduit 44 is bent on a radius of between about 0.22 and 0.40 inches (5.6 mm and 10 mm), and more preferably at about 0.31 inches (7.9 mm).

The area of thickness at the inside or "chin" of the bend 48 strengthens this area while allowing the rest of the cannula's inlet conduit 44 to be made thin in order to maximize the internal cross-sectional area of the cannula inlet conduit 44 while minimizing the external diameter of the cannula inlet conduit 44.

Ordinarily the cannula tip 40 would be produced from the same or similar material as the cannula tube (not shown), which may be either connected or integrally formed with the cannula tip 40. Any suitable bio-compatible material can be used, although polyvinyl chloride (PVC) and other resilient thermoplastic or thermoset materials are considered to be particularly desirable.

Most preferably, the cannula tip 40 is formed of relatively rigid PVC material having a Shore A durometer of approximately 90, and the cannula tube (not shown) of relatively flexible PVC material having a Shore A durometer of approximately 60. This can be accomplished by placing a previously formed cannula tip 40 having the appropriate durometer in a mold (not shown), and injection molding the relatively flexible PVC material in the mold to form the cannula tube extending axially from the body 42 of the cannula tip 40.

As various changes could be made in the above constructions without departing from the scope of the invention, it is intended that all matter contained in the above description or shown in the accompanying drawings shall be interpreted as illustrative and not in a limiting sense.

We claim:

1. An improved arterial cannula tip comprising a hollow tube having a wall forming a bent inlet conduit having a bend and a beveled end portion, the wall of the inlet conduit being thicker at the inside of the bend than in the surrounding areas.

2. The improved arterial cannula tip according to claim 1 wherein the inlet conduit has an average wall thickness of about 0.9 mm, and the area of increased thickness has a thickness of about 1.3 mm.

3. The improved arterial cannula tip according to claim 1 wherein the wall thickness of the inlet conduit is about 40% greater at the inside of the bend than in the surrounding areas.

4. The improved arterial cannula tip according to claim 1 wherein the wall of the inlet conduit is thinner at the outside of the bend than in the surrounding areas.

5. The improved arterial cannula tip according to claim 4 wherein the inlet conduit has an outer surface and an inner surface forming a single lumen, the outer surface and inner surface have generally circular cross sections, with the center of the circular cross section of the inner surface in the area of the bend being offset in the direction away from the inside of the bend relative to the center of the circular cross section of the outer surface.

6. The improved arterial cannula tip according to claim 1 wherein the tip comprises generally resilient thermoplastic or thermoset material.

7. The improved arterial cannula tip according to claim 6 wherein the material of the tip has a Shore A durometer of approximately 90.

8. The improved arterial cannula tip according to claim 7 wherein the wall of the inlet conduit is thinner at the outside of the bend than in surrounding areas.

9. An improved arterial cannula tip of the type comprising a hollow tube having a bent inlet conduit, the improvement comprising constructing the cannula tip so that the wall of the cannula tip is thicker at the inside of the bend than in the surrounding areas by taking a generally tubular blank having an area in which the wall of the blank is thicker than the surrounding areas, and bending the blank in this area of increased thickness.

10. The improved arterial cannula tip according to claim 9 wherein the wall thickness of the blank in the area of increased thickness is about 40% greater than the average wall thickness in the surrounding areas.

11. The improved arterial cannula tip according to claim 10 wherein the tubular blank has a thickness of about 1.3 mm in the area of increased thickness.

12. The improved arterial cannula tip according to claim 9 wherein the wall thickness of the inlet conduit is about 40% greater at the inside of the bend than in the surrounding areas.

13. The improved arterial cannula tip according to claim 12 wherein the cannula inlet conduit has an average wall thickness of about 0.9 mm, and a thickness of about 1.3 mm at the inside of the bend.

14. The improved arterial cannula tip according to claim 9 wherein the cannula tip is constructed so that the wall of the cannula tip is thinner at the outside of the bend than in the surrounding areas.

15. The improved arterial cannula tip according to claim 9 wherein there is an area of decreased wall thickness on the tubular blank opposite the area of increased wall thickness.

16. The improved arterial cannula tip according to claim 15 wherein the blank is formed within a mold having a bent core pin to form the area of increased wall thickness with a smooth contour.

* * * * *